(12) United States Patent
Han et al.

(10) Patent No.: US 7,704,739 B2
(45) Date of Patent: *Apr. 27, 2010

(54) METHOD OF ISOLATING AND CULTURING MESENCHYMAL STEM CELL DERIVED FROM UMBILICAL CORD BLOOD

(75) Inventors: Hoon Han, 521-101, Hanyang APT, Yangji maeul, Soonae-dong, Boondang-gu, Seongnam-si, Gyeonggi-do (KR) 463-922; Sung-Whan Kim, Seoul (KR)

(73) Assignee: Hoon Han, Gyeonggi-do (KR)

( * ) Notice: Subject to any disclaimer, the term of this patent is extended or adjusted under 35 U.S.C. 154(b) by 160 days.

This patent is subject to a terminal disclaimer.

(21) Appl. No.: 10/579,070

(22) PCT Filed: Oct. 25, 2004

(86) PCT No.: PCT/KR2004/002715

§ 371 (c)(1),
(2), (4) Date: May 11, 2006

(87) PCT Pub. No.: WO2005/045010

PCT Pub. Date: May 19, 2005

(65) Prior Publication Data

US 2007/0092967 A1 Apr. 26, 2007

(30) Foreign Application Priority Data

Nov. 11, 2003 (KR) ...................... 10-2003-0079362

(51) Int. Cl.
*C12N 5/00* (2006.01)
*C12N 5/08* (2006.01)

(52) U.S. Cl. .................. 435/378; 435/372; 435/325

(58) Field of Classification Search ................ 435/378, 435/372, 325
See application file for complete search history.

(56) References Cited

U.S. PATENT DOCUMENTS

| 5,197,985 | A | 3/1993 | Caplan et al. | |
|---|---|---|---|---|
| 5,486,359 | A | 1/1996 | Caplan et al. | |
| 6,335,195 | B1 | 1/2002 | Rodgers et al. | |
| 2004/0235160 | A1* | 11/2004 | Nishikawa et al. | .......... 435/370 |

OTHER PUBLICATIONS

Erices et al. Br. J. Hematol. 109:235-242; 2000.*
Petaja et al. J. Clin. Invest. 99:2655-2663; 1997.*
Goodwin et al. Biol. Blood Bone and Marrow Transplant. 7:581-588; 2001.*
Hou, L. et al., "Induction of Umbilical Cord Blood Mesenchymal Stem Cells into Neuron-Like Cells in Vitro", International Journal of Hematology, Oct. 2003, vol. 78 (3), pp. 256-261.
Rooney, P. & Rees, A.A., "Blood Vessel & Mesenchymal Cells: Can They Make Better Bone?" European Cells and Materials, Jun. 2003, vol. 5, Suppl. 2, p. 8.
Haematologica 2001, 86, 1099-100.
Majumdar M.K. et al. 1998, Phenotypic and Functional Comparison of Cultures of Marro-Derived Mesenchymal Stem Cells (MSCs) and Stromal Cells.
Papassavas A.C. et al., 2008, A Strategy of Splitting Individual High Volume Cord Blood Units Into Two Half Subunits Prior to Processing Increases The Recovery of Cells and Facilitates Ex vivo Expansion of the Infused Haematopoietic Progenitor Cells in Adults, International Journal of Laboratory Hematology, 30, 124-132.
Romanov Y.A., 2003, Searching for Alternative Source of Postnatal Human Mesenchymal Stem Cells: Candidate MSC-Like Cells from Umbilical Cord, Stem Cells, 21, 105-110.
Wexler S.A., 2003, Adult Bone Marrow is a Rich Source of Human Mesenchymal 'Stem' Cells But Umbilical Cord and Mobilized Adult Blood Are Not, British Journal of Haematology, 121, 368-274.
Office Action for U.S. Appl. No. 10/579,071 (publ. No. US 2007/0105221) dated Nov. 18, 2008.
Office Action for U.S. Appl. No. 10/579,071 (publ. No. US 2007/0105221) dated May 19, 2008.
National Marrow Donor Program website, www.marrow.org, reference for umbilical cord blood unit transplant information, accessed on Jan. 29, 2009.
New York Blood Center website, www.nationalcordbloodprogram.org, referenced for umbilical cord blood unit information, accessed on Jan. 29, 2009.
Maitra et al., Bone Marrow Transplantation 2004, 33: 597-604.
Yu et al., British Journal of Haematology 2004, 124: 666-675.
Prockop et al., Cytotherapy 2001, 3(5): 393-396.
Non-Hematopoietic Stem Cell Workshop course content, Vancouver, BC, Canada, on Sep. 28, 2008.

* cited by examiner

*Primary Examiner*—Fereydoun G Sajjadi
(74) *Attorney, Agent, or Firm*—Venable LLP; Keith G. Haddaway

(57) ABSTRACT

The present invention relates to a method of isolating and culturing mesenchymal stem cells using umbilical cord blood that is most ideal for cell therapy. The method comprises adding an anti-coagulant to umbilical cord blood having a volume of more than 45 ml per unit, which is obtained within 24 hours after parturition; diluting the resulting mixture of the anti-coagulant and umbilical cord blood with an αMEM (alpha-minimum essential medium), followed by centrifugation to harvest monocytes; and subjecting the obtained monocytes into suspension culture in the αMEM containing Stem Cell Factor, GM-CSF (granulocyte-macrophage colony-stimulating factor), G-CSF (granulocyte colony-stimulating factor), IL-3 (interleukin-3) and IL-6 (interleukin-6).

8 Claims, 2 Drawing Sheets

METHOD OF ISOLATING AND CULTURING MESENCHYMAL STEM CELL DERIVED FROM UMBILICAL CORD BLOOD

TECHNICAL FIELD

The present invention relates to a method for isolating and culturing a mesenchymal stem cell using umbilical cord blood that is most ideal for a cell therapy.

BACKGROUND ART

Mesenchymal stem cells refer to primitive cells that are able to differentiate into bone, cartilage, adipose, nerve and muscle, for example, and are known as being contained in a large amount in bone marrow. In fact, mesenchymal stem cells are presently isolated from bone marrow and then studied for certain purposes or widely used in clinical trials for a variety of diseases.

Although it is easy to obtain mesenchymal stem cells from bone marrow, there are difficulty in acquisition of the bone marrow and further, difficulty to solve problems associated with an immunological rejection reaction occurring when implanting stem cells to others, at present.

Meanwhile, umbilical cord blood is relatively easy to obtain compared with bone marrow, and also, where great numbers of umbilical cord blood units are secured, it is possible to employ umbilical cord blood stem cells that are identical with or most similar to histocompatibility genes of patients and thereby it is possible to solve problems associated with immunological rejection. However, it is relatively difficult to obtain mesenchymal stem cells from umbilical cord blood, as compared to bone marrow and thereby there is difficulty in study and clinical applications.

Conventionally, as a method for isolating very minute amounts of mesenchymal stem cells contained in umbilical cord blood, there has been largely used a method involving separating a leucocyte layer using a density gradient centrifugation method and then culturing cells. However, it is likely to lose cells in the course of a density gradient centrifugation process, thus making it more difficult to culture mesenchymal stem cells that are present in umbilical cord blood in very minute amounts.

As conventional methods of isolating and culturing mesenchymal stem cells, reference may be made to U.S. Pat. Nos. 5,197,985 and 5,486,359, which disclose a method for proliferating mesenchymal stem cells in isolating and purifying mesenchymal stem cells from human bone marrow and cultivating them. That is, U.S. Pat. No. 5,197,985 is directed to a method for inducing human bone marrow-derived mesenchymal stem cells to differentiate into bone-forming cells, comprising: providing human bone marrow-derived mesenchymal stem cells that have been isolated, purified and culturally expanded from a bone marrow specimen by adding the bone marrow specimen to a medium which contains factors which stimulate mesenchymal cell growth without differentiation and allows, when cultured, for selective adherence of only the mesenchymal stem cells to a substrate surface; applying the isolated, purified and culturally expanded human bone marrow-derived mesenchymal stem cells to a porous carrier; and, implanting the porous carrier containing the culturally expanded human bone marrow-derived mesenchymal stem cells into an environment containing factors necessary for differentiating the human mesenchymal stem cells into bone cells, wherein said porous carrier comprises hydroxyapatite and tricalcium phosphate and wherein said medium is comprised of $BGJ_b$ medium with fetal bovine serum (FBS) or is comprised of F-12 Nutrient Mixture. Further, U.S. Pat. No. 5,486,359 discloses isolated human mesenchymal stem cells which can differentiate into cells of more than one tissue type (for example, bone, cartilage, muscle or marrow stroma), a method for isolating, purifying and culturally expanding human mesenchymal stem cells, and characterization of and uses, particularly research reagent, diagnostic and therapeutical uses for such cells. In this patent, mesenchymal stem cells are derived from bone marrow and cultured in $BGJ_b$ medium containing fetal bovine serum.

DISCLOSURE OF INVENTION

Technical Problem

Therefore, the present invention has been made in view of the above problems raised in culturing mesenchymal stem cells, and it is an object of the present invention to provide a reproducible method for isolating and culturing mesenchymal stem cells, in which umbilical cord blood-derived mesenchymal stem cells can be obtained without the loss of cells in the course of density gradient centrifugation.

Technical Solution

In accordance with an aspect of the present invention, the above and other objects can be accomplished by the provision of a method for isolating and culturing mesenchymal stem cells from umbilical cord blood, comprising the steps of:

adding an anti-coagulant to the umbilical cord blood having a volume of more than 45 ml per unit, which is pure umbilical cord blood obtained within 24 hours after parturition;

diluting the resulting mixture of the anti-coagulant and umbilical cord blood with an alpha-minimum essential medium (aMEM), followed by centrifugation to harvest monocytes; and subjecting the obtained monocytes into suspension culture in the aMEM medium containing Stem Cell Factor, GM-CSF (granulocyte-macrophage colony-stimulating factor), G-CSF (granulocyte colony-stimulating factor), IL-3 (interleukin-3) and IL-6 (interleukin-6).

The present invention provides a reproducible method for isolating and culturing mesenchymal stem cells from umbilical cord blood units within 24 hours which was harvested after parturition from a woman delivered of a child. That is, it is intended to contribute to treatment of intractable diseases using umbilical cord blood, by finding out optimum conditions for isolating and culturing mesenchymal stem cells from umbilical cord blood relatively lacking the number of cells.

In order to achieve this purpose, the present invention is completed by diluting umbilical cord blood with 2-fold volume of aMEM medium, followed by centrifugation so as to harvest a monocyte layer, and then culturing monocytes in the aMEM medium to which cell growth factors, Stem Cell Factor, GM-CSF, G-CSF, IL-3 and IL-6 were added, thereby making it possible to secure primitive mesenchymal stem cells and improve a success rate of cell culture up to about 90% from less than of 10% obtained in a conventional method.

DESCRIPTION OF THE DRAWINGS

The above and other objects, features and other advantages of the present invention will be more clearly understood from the following detailed description taken in conjunction with the accompanying drawings, in which.

BEST MODE

Now, a method for isolating and culturing mesenchymal stem cells from umbilical cord blood in accordance with the present invention will be described in more detail with reference to the following Examples. These examples are provided only for illustrating the present invention and should not be construed as limiting the scope and sprit of the present invention.

EXAMPLES

Example 1

Isolation and Culture of Mesenchymal Stem Cells

In order to isolate monocytes from umbilical cord blood, the umbilical cord blood was diluted with two-fold volume of aMEM (alpha-minimum essential medium, Jeil Biotech Services, Korea), transferred to a 50 ml Falcon tube and centrifuged at 300×g, at room temperature for 10 min. The separated buffy coat layer was collected, diluted again with two-fold volume of aMEM, overlapped on Ficoll-Hypaque and centrifuged at 300×g, at room temperature for 30 min.

In separating monocytes from blood, Ficoll-Hypaque, which is a polymer of Ficoll (a polymer of sucrose) and Hypaque (sodium ditrizoate), is largely used. Ficoll-Hypaque has a specific gravity of 1.077 g/ml, which is heavier than that of monocytes, but lighter than that of red blood cells, thus making it possible to separate from each other by specific gravity difference therebetween. That is, when blood is placed on Ficoll-Hypaque and centrifuged, monocytes are gathered on Ficoll-Hypaque.

Monocytes obtained by such a density gradient centrifugation method were placed again in a washing aMEM in which additives had not been mixed and centrifuged at 200×g, for 10 min, and thereafter, aMEM was discarded and washed, except for cells sedimented at the bottom of the Falcon tube. aMEM was added thereto once again, centrifuged at 200×g for 10 min, and thereafter, aMEM was discarded and washed one more time, except for cells sedimented at the bottom of the Falcon tube.

Next, to aMEM medium containing an antibiotic (1000 U/ml penicillin G, 1000 μg/ml Streptomycin sulfate, Gibco-BRL) and an anti-fungal agent (0.25 μg/ml Amphotericin B), and 2 mM of Glutamine (Sigma) were added 20% fetal bovine serum (FBS, Jeil Biotech Services, Korea) and as cell growth factors, Stem Cell Factor (50 ng/ml), GM-CSF (granulocyte-macrophage colony-stimulating factor; 10 ng/ml), G-CSF (granulocyte colony-stimulating factor; 10 ng/ml), IL-3 (interleukin-3; 10 ng/ml) and IL-6 (interleukin-6; 10 ng/ml), and cells were suspended in concentration of $1 \times 10^6/cm^2$.

Suspending cells were removed from 5-day cultured cell group, and after adherent cells were secured, they were cultured for 25 days in aMEM containing an 20% fetal bovine serum and an antibiotic as a culture medium, with complete replacement of culture medium at intervals of 2 days without a washing process.

Figure 1:
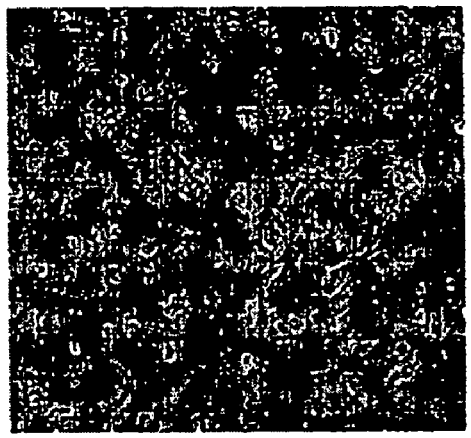
FIGS. 1 through 5, respectively, are photographs (×100) showing results after culturing an umbilical cord blood mesenchymal stem cell line, for 5, 7, 10, 15 and 25 days, in accordance with a method of the present invention.
Figure 2:
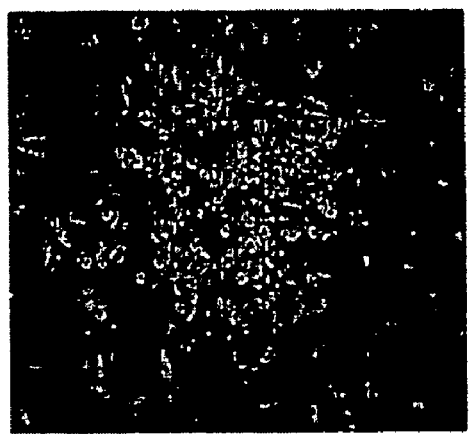
Figure 3:
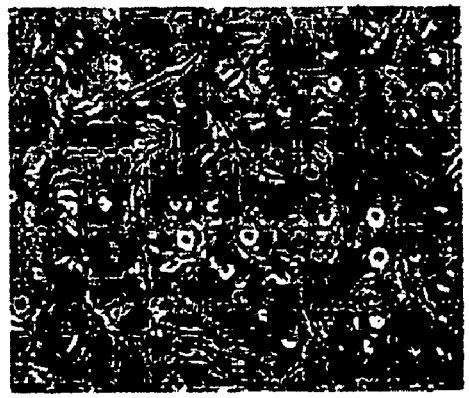
Figure 4:
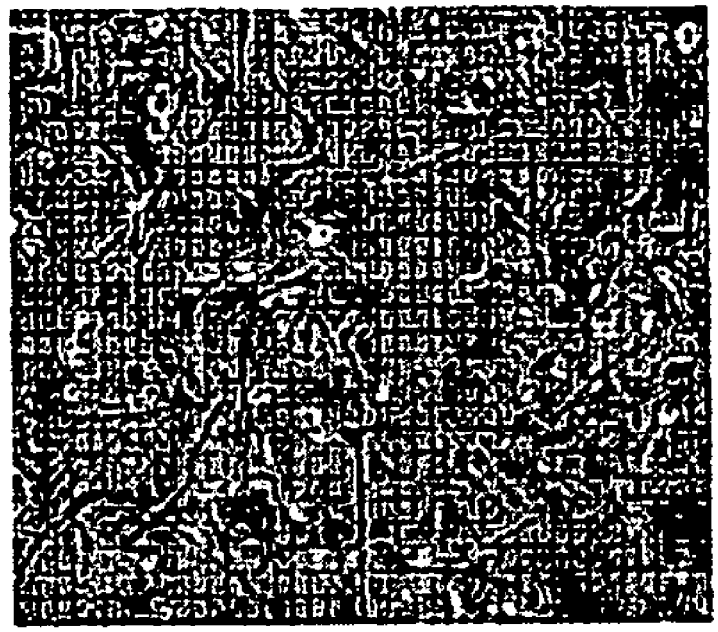
Figure 5:
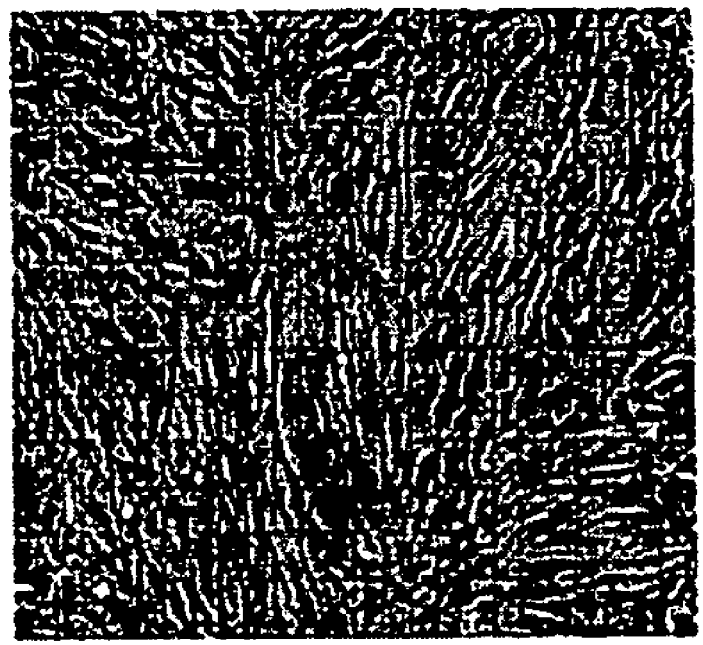

FIGS. 1 through 5, respectively, are photographs (×100) showing results observed after culturing an umbilical cord blood mesenchymal stem cell line, for 5, 7, 10, 15 and 25 days, in accordance with a method of the present invention. As can be seen, when monocytes isolated from umbilical cord blood were cultured, cells adhering to and growing at the bottom of the flask were observed 5 days after culturing and on day 7, cells formed colonies and then grown to cells having various shapes. 10 days after culturing, monocytes undergoes differentiation into spindle-shaped cells, and 25 days after culturing, these spindle-shaped cells become complete mesenchymal stem cells through cell division and multiplication, thereby completing culturing.

Example 2

Characterization of a Cell Surface Antigen of Cultured Mesenchymal Stem Cells

In order to examine characteristics of a cell surface antigen of spindle-shaped mesenchymal stem cells isolated and cultured as described above, the cell surface antigen was analyzed by FACS. The results are shown in Table 1 below. FACS (fluorescence activated cell sorting; a flow cytometer) may analyze characteristics of cells of interest by attaching a luminescent immune antigen indicator to the surface thereof, or may separate only cells having a certain antigen indicator depending on desired purposes.

TABLE 1

| Indicator | Reaction |
|---|---|
| CD14 | − |
| CD34 | − |
| CD45 | − |
| SH2 | + |
| SH3 | + |
| C29 | + |
| CD44 | + |
| CD90 | + |
| CD166 | (+) |

It was confirmed from Table 1 that in the case of stem cells isolated and cultured in accordance with the present invention, CD34, CD45 and CD14, which are characteristic indicators of hematopoietic stem cells, showed negative reactions, SH2, SH3, CD29 and CD44, which are characteristic indicator of mesenchymal stem cells, showed positive reactions, and CD166 showed a weak positive reaction. This fact is interpreted as showing that cells isolated and cultured in accordance with the present invention are mesenchymal stem cells.

Example 3

Comparison of Success Rate of Mesenchymal Stem Cell Culture 50 units of umbilical cord blood were cultured according to a conventional method and the method of the present invention, respectively, and success rates of cell culture were compared therebetween. The results are shown in Table 2 below.

Specifically, in the conventional method, umbilical cord blood was used in stem cell culturing, without criteria on an amount of umbilical cord blood to be used and a period from parturition to harvesting. Further, the conventional method did not include cell growth factors in a culture medium, and except for that point, an isolating process of cells was performed similar to the method in accordance with the present invention.

TABLE 2

|  | Conventional | Inventive |
|---|---|---|
| Number of mesenchymal stem cell units acquired | 1 | 49 |
| Success rate of culturing (%) | 2 | 98 |

As can be seen from Table 2 above, upon comparing success rate of mesenchymal stem cell culture, the conventional method showed a success rate of 2%, while the present invention showed a high success rate of 98%.

INDUSTRIAL APPLICABILITY

As described above, in accordance with the present invention, it is possible to effectively isolate and culture mesenchymal stem cells from umbilical cord blood relatively lacking the number of cells, and thus umbilical cord blood which is wastefully disposed without use thereof may be employed as an important means for curing a variety of intractable diseases as cell therapy.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method for isolating and culturing mesenchymal stem cells from umbilical cord blood, comprising the steps of:
   adding an anti-coagulant to pure umbilical cord blood obtained within 24 hours after parturition;
   diluting the resulting mixture of the anti-coagulant and umbilical cord blood with an alpha-minimum essential medium (aMEM), followed by centrifugation to harvest monocytes; and
   subjecting the obtained monocytes into suspension culture in the aMEM medium containing Stem Cell Factor, GM-CSF (granulocyte-macrophage colony-stimulating factor), G-CSF (granulocyte colony-stimulating factor), IL-3 (interleukin-3), and IL-6 (interleukin-6).

2. The method as set forth in claim 1, wherein the umbilical cord blood is diluted with 2-fold volume of the aMEM medium, overlapped on Ficoll-Hypaque and subjected to centrifugation so as to harvest monocytes.

3. The method as set forth in claim 1, wherein aMEM medium for culturing monocytes further comprises at least one of an antibiotic, an anti-fungal, glutamine and fetal bovine serum.

4. The method as set forth in claim 3, wherein the aMEM for culturing monocytes further comprises an antibiotic, an anti-fungal agent, glutamine and fetal bovine serum.

5. The method as set forth in claim 1, wherein the umbilical cord blood has a volume of more than 45 ml per unit.

6. The method of claim 3, wherein the antibiotic is selected from penicillin G, streptomycin sulfate, or a combination thereof.

7. The method of claim 3, wherein the antifungal agent is amphotericin B.

8. The method of claim 1, wherein the isolated mesenchymal stem cells are negative for CD14, CD34, CD45 indicators and are positive for SH2, SH3, CD29, CD44, CD90, and CD166 indicators.

* * * * *